(12) United States Patent (10) Patent No.: US 8,045,263 B2
Yaroslavsky et al. (45) Date of Patent: Oct. 25, 2011

(54) DEVICE AND METHOD FOR WIDE-FIELD AND HIGH RESOLUTION IMAGING OF TISSUE

(75) Inventors: Anna M. Yaroslavsky, N. Andover, MA (US); Robert H. Webb, Lincoln, MA (US); Richard R. Anderson, Boston, MA (US)

(73) Assignee: The General Hospital Corporation, Boston, MA (US)

(*) Notice: Subject to any disclaimer, the term of this patent is extended or adjusted under 35 U.S.C. 154(b) by 506 days.

(21) Appl. No.: 11/823,610

(22) Filed: Jun. 28, 2007

(65) Prior Publication Data

US 2008/0024860 A1 Jan. 31, 2008

Related U.S. Application Data

(60) Provisional application No. 60/818,200, filed on Jun. 30, 2006.

(51) Int. Cl.
*G02B 21/06* (2006.01)
*G02B 21/00* (2006.01)

(52) U.S. Cl. ........................ 359/385; 359/368

(58) Field of Classification Search .......... 359/368–390, 359/819
See application file for complete search history.

(56) References Cited

U.S. PATENT DOCUMENTS

| | | | |
|---|---|---|---|
| 3,970,841 A * | 7/1976 | Green | 250/548 |
| 4,676,608 A * | 6/1987 | Faubion | 359/383 |
| 5,127,726 A * | 7/1992 | Moran | 356/237.2 |
| 5,381,224 A | 1/1995 | Dixon et al. | |
| 5,836,877 A | 11/1998 | Zavislan | |
| 5,991,038 A * | 11/1999 | Yamamoto | 356/600 |
| 6,459,493 B1 * | 10/2002 | Sugiura et al. | 356/630 |
| 6,462,345 B1 * | 10/2002 | Simon et al. | 250/458.1 |
| 6,867,862 B2 * | 3/2005 | Nikoonahad | 356/340 |
| 7,329,859 B2 * | 2/2008 | Mizutani et al. | 250/231.13 |

(Continued)

FOREIGN PATENT DOCUMENTS

EP 0228493 A1 7/1987

(Continued)

OTHER PUBLICATIONS

International Search Report for the corresponding international application No. PCT/US07/15277, filed Feb. 8, 2008.

(Continued)

*Primary Examiner* — Thong Nguyen
(74) *Attorney, Agent, or Firm* — Edwards Angell Palmer & Dodge LLP; Peter C. Lauro, Esq.; George N. Chaclas, Esq.

(57) ABSTRACT

A device for wide-field and high resolution imaging of an object surface includes first and second imaging modalities, a lens associated with the second imaging modality. The first imaging modality is high resolution with a first observation line. The second imaging modality is arranged in an image plane at a first angle with respect to an object plane and has a second observation line and a wider imaging field than the first imaging modality. The lens associated with the second imaging modality is arranged in a lens plane at a second angle with respect to the object plane, where the second angle being equal to about one-half of the first angle. The first and second imaging modalities are mutually arranged such that the first and second optical axes intersect at a point on the object plane.

23 Claims, 3 Drawing Sheets
(1 of 3 Drawing Sheet(s) Filed in Color)

U.S. PATENT DOCUMENTS

| | | |
|---|---|---|
| 2004/0133112 A1 | 7/2004 | Rajadhyaksha |
| 2004/0136582 A1 | 7/2004 | Bacus et al. |
| 2005/0157294 A1 | 7/2005 | Hopkins et al. |
| 2006/0011725 A1 | 1/2006 | Schnee |
| 2006/0132790 A1 | 6/2006 | Gutin |

FOREIGN PATENT DOCUMENTS

| | | |
|---|---|---|
| JP | 2005 118133 A | 5/2005 |
| JP | 2006 039048 A | 2/2006 |
| WO | 2006076810 A1 | 7/2006 |
| WO | WO 2008/005402 A2 | 1/2008 |

OTHER PUBLICATIONS

Written Opinion of the corresponding international application No. PCT/US07/15277, filed Feb. 8, 2008.

Rajadhyaksha M. Anderson RR, Webb RH: Video-rate confocal scanning laser microscope for imaging human tissues in vivo. *Appl. Opt.* 10:2105-2115, 1999.

Wagnieres, G. Star W, Wilson BC: In vivo fluorescence spectroscopy and imaging for oncological applications. *Photochem. Photobiol.* 68:603-632.1998.

Boppart, SA, Bouma BE, Pitris C, Tearney GJ, Southern JF, Brezinski ME, Fujimoto JG: Intraoperative assessment of microsurgery with three-dimensional optical coherence tomography, *Radiology.* 208:81-6, 1998.

New KC, Petroll WM, Boyde A et al.: In vivo imaging of human teeth and skin using real-time confocal microscopy. *Scanning* 13:369-372, 1991.

Rajadhyaksha M, Grossman M, Esterowitz D, Webb RH, Anderson RR: In vivo confocal scanning laser microscopy of human skin: melanin provides strong contrast. *J. Invest. Dermatol.* 104:946-952, 1995.

Rajadhyaksha M, Menaker G, Dwyer PJ, Flotte TJ, Gonzalez S: Confocal examination of nonmelanoma cancers in skin excisions to potentially guide Mohs micrographic surgery without frozen histopathology. *J. Invest. Dermatol.* 117:1137-1143, 2001.

Yaroslavsky AN, Neel V, Anderson RR. Demarcation of nonmelanoma skin cancer margins using multi-spectral polarized-light imaging. *J. Invest. Dermatol.* 121:259-266, 2003.

Oseroff AR, Ohuoha D, Ara G, McAuliffe D, Foley J. Cincotta L: Intramitochondrial dyes allow selective in vitro photolysis of carcinoma cells. *Proc. Natl. Acad. Sci. USA*, 83:9729-9733, 1986.

EPO Form 1507S, Mar. 9, 2010, Extended European Search Report for 07810105.2.

* cited by examiner

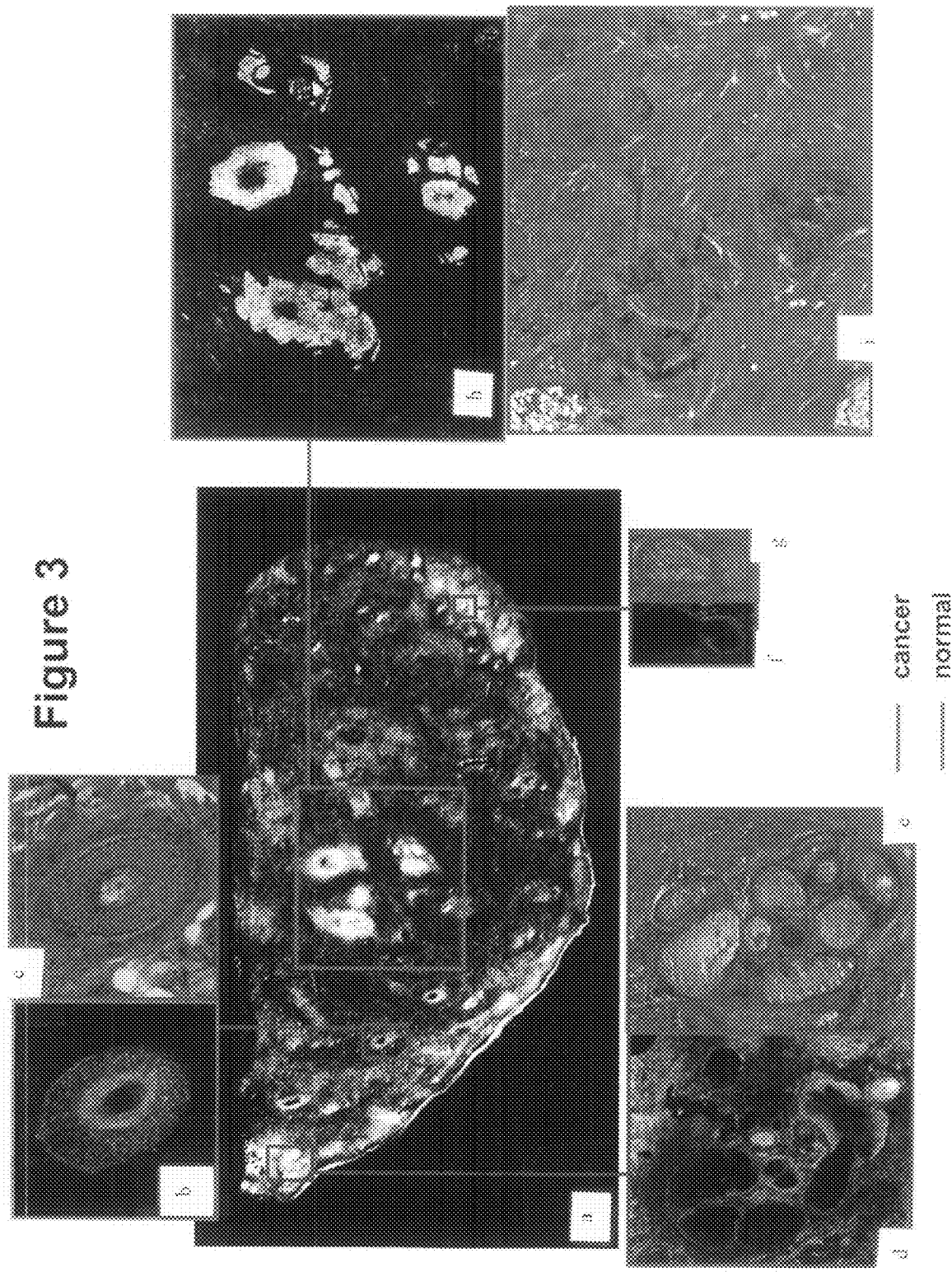

DEVICE AND METHOD FOR WIDE-FIELD AND HIGH RESOLUTION IMAGING OF TISSUE

CROSS-REFERENCE TO RELATED APPLICATION

This application claims priority to U.S. Provisional Patent Application No. 60/818,200 filed Jun. 30, 2007, which is incorporated herein by reference.

This invention was made with Government support under Grant No. EB002423 awarded by the National Institutes of Health. The Government has certain rights in the invention.

BACKGROUND OF THE INVENTION

1. Field of the Invention

The present invention relates to a device and method for wide-field and high resolution imaging. Particularly, the present invention is directed to a system having wide-field and high resolution imaging capability.

The present invention is particularly suitable for imaging skin cancer, e.g., as a rapid bedside guide to tumor excision. The invention is useful for providing enhanced imaging of epithelial tumors, inflammatory disorders, or other pathological conditions, including nonmelanoma skin cancer. However, the subject device and method may be used for imaging and analyzing surface, structural, spectral, functional, fluorescence, Raman, bio-chemical, polarization and other similar characteristics of any object when the combination of wide field imaging and high resolution is required.

2. Description of Related Art

Advances in the development of optical imaging modalities have facilitated efforts to employ these techniques for noninvasive detection and treatment guidance of different pathological conditions. In general, the turbidity of tissue creates major challenges for optical in vivo spectroscopy and imaging. However, reflectance and fluorescence imaging techniques, like multi-spectral polarized light macro-imaging and confocal microscopy are well suited for skin cancer detection and demarcation. Confocal reflectance microscopy was introduced to the field of dermatology in the 1990s. Since then, it has been used to study different skin disorders.

Confocal microscopy is a technique where the specimen is pointwise illuminated by a focused beam of light. An image is recorded by scanning the beam focus through a plane in the specimen, and the reflected light from the specimen is focused onto a small detector aperture. The light source, the illuminated spot and the detector aperture are placed in optically conjugated focal planes. "Optical sectioning" occurs as out-of-focal-plane back-scattered light is rejected by a pinhole placed in front of a detector. Optical sectioning makes it possible to record images of thin layers within tissue. Confocal microscopy allows imaging within turbid media with high resolution (lateral resolution of about 1 $\mu$m, and axial resolution (section thickness) of about 3-5 $\mu$m), which is comparable to histology. The major disadvantage of confocal microscopy as a detection and guidance tool for cancer surgery is its small field of view, which is typically, up to about 0.3 mm. To examine an entire suspected cancerous area using confocal microscopy (CM), a sequence of images must be captured and stitched together. This process takes time and motion artifacts may distort the resulting image.

Multi-spectral polarized light imaging (MSPLI) is a simple and inexpensive technique for skin tumor imaging. The technique provides the means to differentiate effectively between endogenous (blood, melanin, etc.) and exogenous (dye) chromophores absorbing in different spectral domains, and is capable of obtaining superficial images (at a resolution of about 3-50 $\mu$m-lateral, 5-0200 $\mu$m-axial in the visible spectral range) of thick tissue layers. Such imaging is relatively insensitive to small shifts in the position of the imaged object, and combination of the large field-of-view and sufficient lateral resolution enables rapid examination of large surfaces, thus facilitating tumor margin delineation. However, morphology of individual cells and fine structures cannot be resolved using MSPLI. Thus, the multi-spectral polarized light imaging approach can benefit from combination with a high-resolution technique, such as confocal reflectance microscopy, which can be used by a pathologist in the cases when high-resolution images of small suspicious areas are required. Such combination may become a powerful tool for cancer detection and demarcation.

SUMMARY OF THE INVENTION

The purpose and advantages of the present invention will be set forth in and apparent from the description that follows. Additional advantages of the invention will be description and claims hereof, as well as from the appended drawings.

The present technology relates to a novel device that combines a wide-field, low-resolution imaging modality and a high-resolution, narrow-field imaging modality, which preferably share a common light source and hardware control unit. One preferred embodiment includes a combination of confocal microscopy with wide-field CCD (charge-coupled device) imaging. By combining these two imaging devices, a high resolution wide-field imaging is effectively achieved. CCD imaging, for example, the technique of multi-spectral polarized light imaging (MSPLI), enables rapid inspection of a superficial tissue layer over large surfaces, but does not provide information on cellular microstructure. Confocal microscopy (CM) allows imaging within turbid media with resolution comparable to that of histology, but suffers from a small field of view. Typically, pathologists use microscopes at low power and high power, to view the margins of pathology and cell features, respectively. Therefore, the present technology, which can combine, for example, MSPLI and CM can guide cancer surgery more rapidly, and at lower cost than conventional histopathology.

To achieve these and other advantages and in accordance with the purpose of the subject technology, as embodied, the subject technology includes a device for wide-field and high resolution imaging of an object surface includes first and second imaging modalities, a lens associated with the second imaging modality. The first imaging modality has a high resolution imaging means with a first observation line, such as an optical axis in the event that the imaging modality is optical. It will be understood that non-optical imaging modalities can also be used including but not limited to acoustic (e.g., ultrasonic), terahertz and the like, for example.

The second imaging modality is arranged in an image plane at a first angle with respect to an object plane and has a second observation line and a wider imaging field than the first imaging modality. The lens associated with the second imaging modality is arranged in a lens plane at a second angle with respect to the object plane, where the second angle being equal to about one-half of the first angle. The first and second imaging modalities are mutually arranged such that the first and second optical axes intersect at a point on the object plane.

The first imaging modality can include a confocal microscope including an objective lens, a multi-photon microscope, a high-resolution CCD imaging device or another high-resolution imaging device.

Devices in accordance with the present technology can be capable of adjusting to a first configuration, in which the second imaging modality is capable of capturing an image and/or to a second configuration, in which the first imaging modality is capable of capturing a high-resolution image. The first imaging modality can be capable of imaging both an object surface as well as beneath the object surface. The first and second imaging modalities can be supported by a supporting structure, such supporting structure providing rigidity, providing support to the device components, and/or enabling the device to be moved with respect to the object surface. The second modality and the lens can be pivotally supported by the device.

It is to be understood that both the foregoing general description and the following detailed description are exemplary and are intended to provide a non-limiting explanation of the subject technology.

BRIEF DESCRIPTION OF THE DRAWINGS

The patent or application file contains at least one drawing executed in color. Copies of this patent or patent application publication with a color drawing(s) will be provided by the Office upon request and payment of the necessary fee.

The accompanying drawings, which are incorporated in and constitute part of this specification, are included to illustrate and provide a further understanding of the method and system of the invention.

FIG. 3 is a series graphic representations, a-i, of exemplary image outputs from a system in accordance with the present technology.

DETAILED DESCRIPTION OF THE PREFERRED EMBODIMENT

Reference will now be made in detail to the present preferred embodiments of the invention, an example of which is illustrated in the accompanying drawings. The method and corresponding steps of the subject technology will be described in conjunction with the detailed description of the system.

Figure 1:
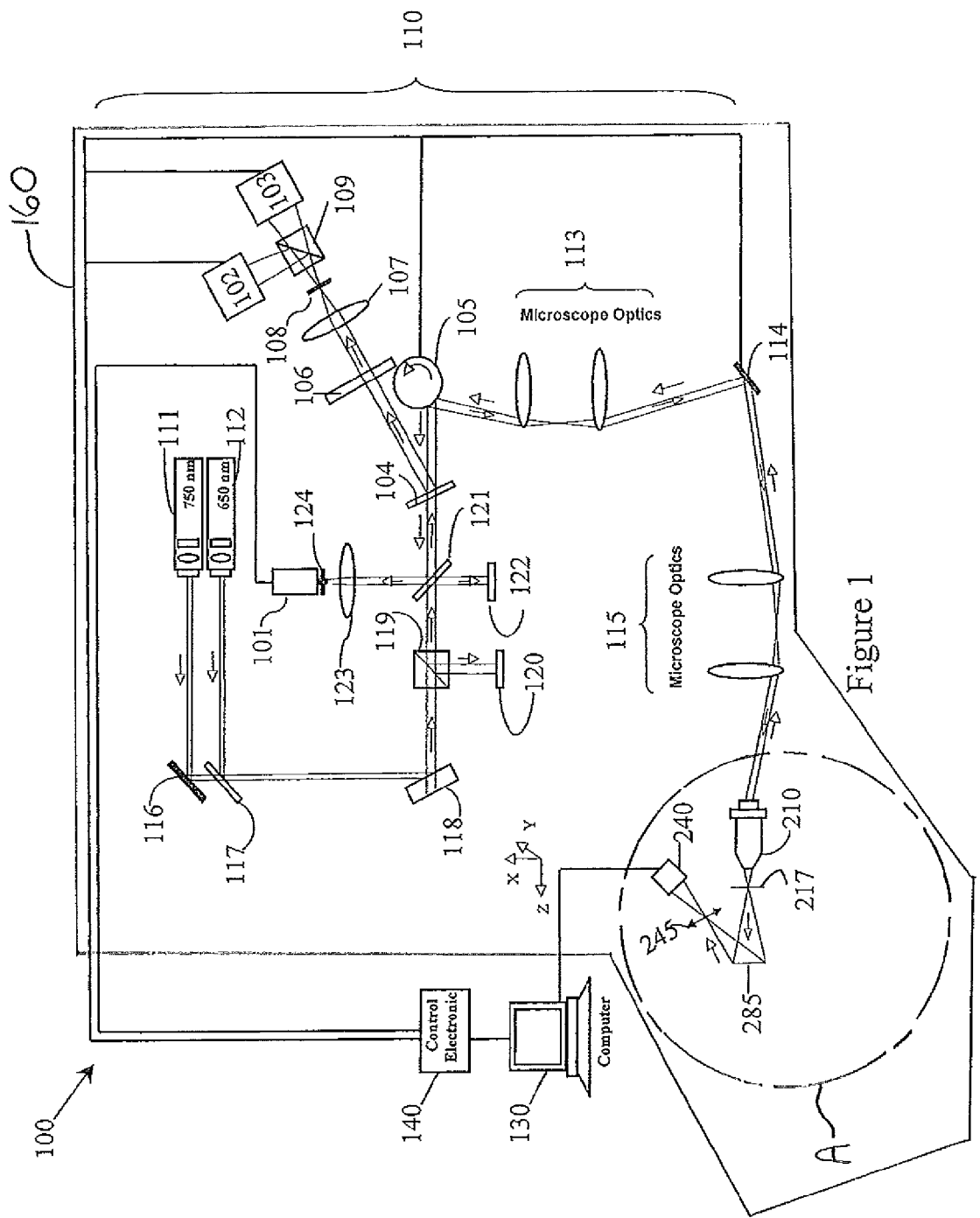
FIG. 1 is a schematic layout of a multimodal wide-field, high-resolution imaging system in accordance with the present technology.
Figure 2:
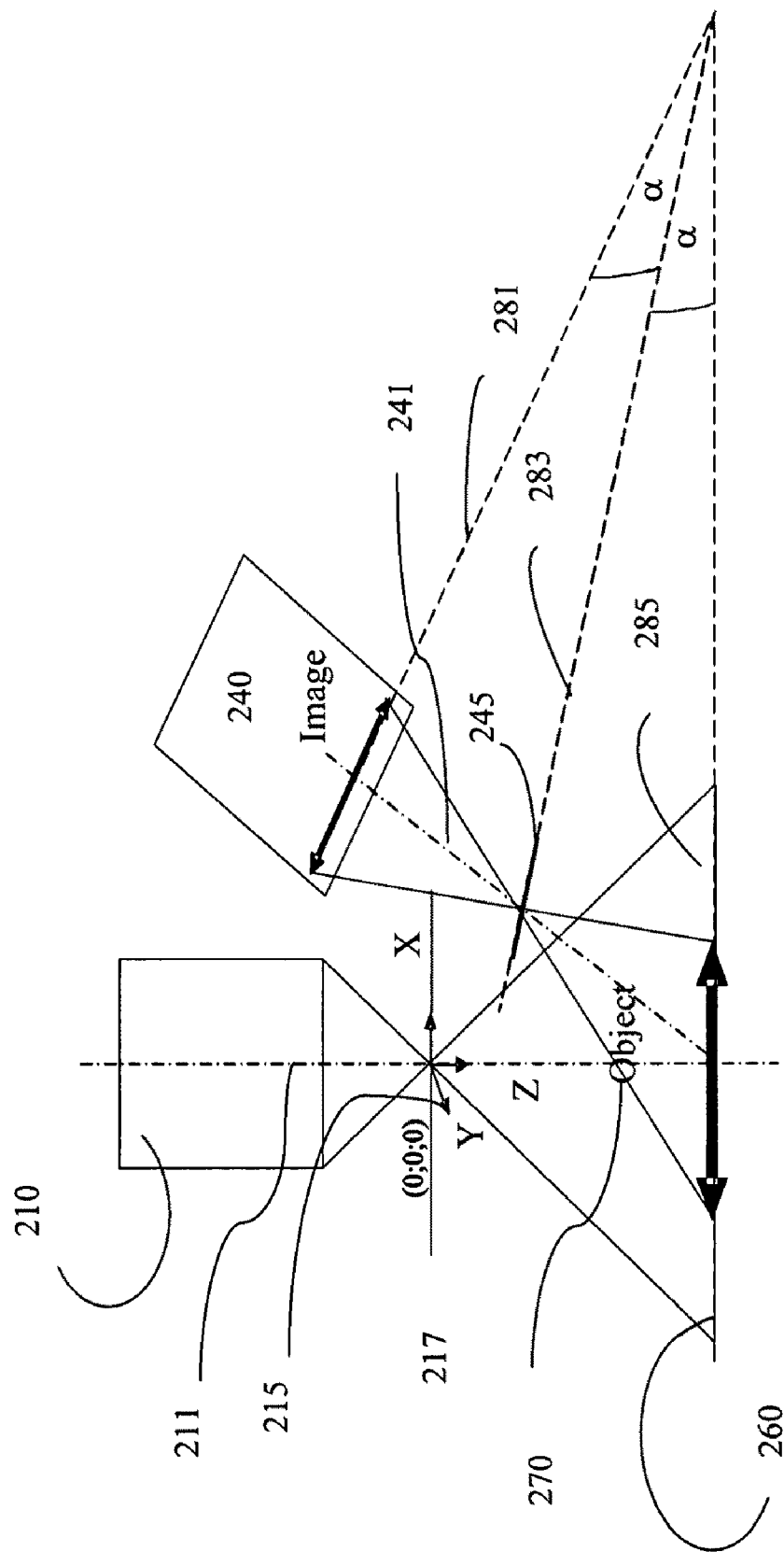
FIG. 2 is a schematic representation of an optical layout from box A of FIG. 1.

For purpose of explanation and illustration, and not limitation, a view of an exemplary embodiment of a system 100 in accordance with the present technology is illustrated in FIG. 1. FIG. 2 illustrates in more detail the optical layout within region A of FIG. 1.

The present technology includes both a device and a method for effectively obtaining high-resolution wide-field optical imagery, which cannot be achieved with previously known devices or methods. This is achieved by combining a pair of imaging modalities: a wide-field relatively low-resolution imaging modality and a high-resolution, relatively narrow-field imaging modality, which preferably share a common light source. Either monochromatic or polychromatic light source can be employed, including, but not limited to, lasers, LEDs, discharge lamps, incandescent lamps, and the like. The illumination wavelength can be in the range between 10 nm and 1 mm. The detected radiation can be elastically scattered, fluorescent, Raman, non-linearly formed (e.g., second harmonic), or generated as a result of another physical phenomenon in the imaged object.

In one preferred embodiment, the wide-field modality is polarization-enhanced elastic/fluorescent imaging with a CCD sensor, and the high-resolution modality is confocal microscopy. Both modes can be controlled by a computer or a similar control device. In such an arrangement, the user is preferably able to switch seamlessly between the first and second imaging modalities. The high-resolution modality can be automatically positioned at the point of interest selected by the user within the field-of-view of the wide-field modality, with subsequent image acquisition by the high-resolution modality from a region near that point. Alternatively, the point of interest to be imaged with the high-resolution imaging modality can be automatically selected by a computer, based on predetermined identifiable characteristics, such as predetermined surface features.

FIG. 1 illustrates a schematic of an example embodiment of a system in accordance with the subject technology. In this exemplary embodiment, an advantage achieved by combining the macroscopic and confocal imaging into a single unit with common illumination, image acquisition, and hardware control, is the ability to rapidly inspect large surfaces. Based on the analysis of macroscopic images, if necessary, one can zoom-in and acquire (automatically or manually), narrow-field, high-resolution confocal images of the desired regions, such as suspicious parts of a skin lesion of a patient. The time required for the detection of tumor margins and small tumor nests is thus dramatically reduced as compared with existing devices and methods.

Further, if embodied with automatic positioning capability, devices in accordance with the subject technology can precisely automatically center the high-resolution imaging modality, such as a confocal imaging system, at the area of interest selected by analyzing an image captured with the wide-field imaging modality. Accuracy of tissue discrimination will therefore be significantly improved.

With reference to the system 100 as depicted in FIG. 1, the illumination for both macro and confocal imaging is preferably provided by the same source or sources of light, such as by diode lasers 111, 112. In general, light of any wavelength in a range from about 190 nm to about 2600 nm can be used. However, when used for tumor delineation, lasers 111, 112 emitting linearly polarized light at the wavelengths of 650 nm and 750 nm, respectively can be used. Light having a wavelength of 650 nm lies within the absorption band of Methylene Blue (MB) contrast agent, and light of wavelength of 750 nm is a reference wavelength outside the absorption band of MB. In the confocal optical subsystem 110 of system 100, a polarizing beam splitter 119 further increases the degree of linear polarization of the light incident on the tissue. For simultaneous registration of the reflectance and fluorescence images, a 90/10 non-polarizing beam splitter 121 is installed after the polarizing beam splitter 119. Beam stops 120 and 122 are provided, as needed. As set forth above, the confocal optical subsystem 110 can instead be replaced any suitable high-resolution imaging device. Such devices can include, but are not limited to a multi-photon microscope or a high-resolution CCD device, for example.

In the embodiment of FIG. 1, the optical components are mounted in a supporting structure 160. The lens 217 and the CCD device 240, among other components, may be mounted in the supporting structure 160 for movement, including pivotal, within the supporting structure 160. For fluorescence imaging, a purpose-designed, 12° dichroic mirror 104 is placed in the optical path of light coming from the objective 210 of the microscope 110. An additional filter 106 selects a narrow 690±10 nm band from the fluorescence signal. The collimated fluorescence beam is then focused onto a pinhole 108. Two orthogonal fluorescence polarization states are separated by a polarizing beam splitter 109 and are registered simultaneously by two identical balanced photomultiplier tubes 102, 103. An electronic control unit 140 and/or computer 130 allows simultaneous signal processing from three PMT units 101, 102 and 103. Preferably, a pinhole 124 is placed before the PMT unit 101. For macro-imaging, a diverging light beam can be delivered through the objective 210 of the confocal microscope 110 and used to perform wide-field illumination for the imaging of the CCD device 240. Alternatively, a separate illumination device can be utilized—one which does not deliver illumination through confocal optics 113, 115 of a confocal microscope 110. The confocal optics of the confocal imager, as embodied in FIG. 1, can further include various minors 114, 116, 117, 118, lenses 123, 107, and filters (e.g., 106), as needed. A polygon mirror 105 is also provided. A confocal microscope is described in U.S. Pat. No. 5,381,224 to Dixon et al., which is hereby incorporated by reference in its entirety.

Reflectance and fluorescence macroscopic images can be acquired using the CCD device 240, which can be coupled to an image-splitter, such as a 4-band image-splitter, and can be operatively associated with a macro-lens 245 (FIG. 2). The layout of the CCD device 240 and lens 245, as best seen in FIG. 2, allows a variable angle of light incidence onto the amplitude beam splitter coupled to the CCD device 240. CCD positioning in an image plane 281, at an angle of 2α with respect to the object plane 285, would typically result in the distortion of a captured image. Such distortion can be minimized by placing the CCD imaging lens 245 at the bisection of the angle (2α) formed between the object plane and image plane, or at about an angle of α.

In one preferred embodiment, positioning a CCD device 240 at a 55° angle, and the CCD lens 245 at a 27.5° angle, each with respect to the object plane 285, significantly improves the image quality (see object b of FIG. 3) as compared to an image obtained with a lens positioned in the same plane, as a CCD device image plane 281 (see object a of FIG. 3).

A 4-band amplitude image splitter (not shown) can be employed for simultaneous reflectance and fluorescence polarization image acquisition, via a single or multiple CCD devices or other sensors, as desired. The image splitter can include a collimating lens, to collimate the light coming from an intermediate image, a four-sided highly reflective pupil separating pyramid prism, to split the incident beam in four, and four adjustable mirrors to fold the beams through the optical system (not shown). The purpose of the splitter is to simultaneously produce four images of the object being imaged. The image splitter eliminates artifacts in difference images due to fluctuations of lamp intensity and patient motion, as well as speeding up the image acquisition process. Linearly polarizing filters, neutral density filters, and/or spectral bandpass filters can be introduced into the optical paths of the four spatially-separated beams to study reflectance, fluorescence, and polarization images of the tissue, as desired. Additionally or alternatively, other imaging techniques, such as Raman, multi-photon and harmonic generation imaging techniques can be used.

Moreover, for optimal image acquisition and processing it is preferred that the intensity scales of the reflectance and fluorescence channels do not differ substantially. Reflectance and fluorescence channels can be balanced by the introduction of the neutral density filters into the optical path of reflectance channels. However, throughput of two reflectance and/or two fluorescence channels may vary. To account and compensate for such potential differences at the image processing stage, a calibrated reflectance/fluorescence reference can be placed in the camera field of view. Specifically, a reference sample can be kept in the camera's field of view to account for fluctuations in light and the like. Lateral resolution and the field of view can be controlled by the magnification lenses. Multiple interchangeable lenses can be utilized to allow different magnifications, depending on the dimensions of the area or region under investigation. The macro-imaging field of view is preferably about 20-30 mm (with lateral resolution not worse than 60 μm).

Image acquisition and analysis is accomplished as follows. First, macro-images are acquired. Then, the macro-images are inspected by a physician or an investigator who creates a list in a computer memory or otherwise notes suspicious areas that require closer inspection by, for example, confocal imaging. Such listing can be achieved by pointing at the desired regions using a computer input device such as a mouse, touch screen or digitizing pad, for example. Alternatively, such images can be analyzed and listed by a computer system, based on predetermined search characteristics, such as image characteristics corresponding to a particular type of skin cancer.

As shown in FIG. 2, the intersection of an observation line (or optical axis, depending on the frequency regime in which the system is chosen to operate) 211 of the confocal system 110 with the confocal imaging plane 217 can be used to define the (0;0;0) point 215 of a Cartesian system of coordinates, so that the (x;y;z) coordinates of the areas of interest can be easily determined using computer code. A translation stage 260, which can be provided, can be capable of movement in three dimensions. Alternatively, if desired, the imager device itself can be automatically moved to the corresponding areas of interest on the object to be imaged. The object to be imaged can be, for example, a patient's skin. Subsequently, reflectance, fluorescence, and fluorescence polarization images for each location of interest are acquired and displayed side by side with macro-images, and can be analyzed. Such images can be acquired via a confocal optical system, if the device and system are so-equipped. An example of combined images, a-f, is presented in FIG. 3.

As can be seen in FIG. 2, when the device 100 is configured to image a region with the wide-field imaging modality, via CCD device 240, the relative orientation of the observation line (e.g., optical axis) 241 of the CCD device 240 and the observation line 211 of the high-resolution imaging device 110 is known. Preferably, such axes intersect at about the surface of the object to be imaged. Naturally, the device can be adjusted as needed.

If the imaging devices 110 and 240 need to be repositioned with respect to the object surface 270, such movement can be achieved automatically or manually, by an operator. Both imaging modalities are preferably supported by a common physical structure to enable movement over the object surface. Moreover, since the lens 245 and its plane 283 preferably bisect the angle between the object plane 285 and the CCD image plane 281, such adjustment would require adjustment of the angles of the lens 245 and CCD device 240. Accordingly, these elements are preferably pivotally mounted with respect to the aforementioned structure.

Further, since the embodiment of FIGS. 1 and 2 includes illumination provided via confocal optics 113, 115, the objective 210 of the confocal microscope must be capable of adjusting in the Z-axis direction in order to both provide illumination for the wide-field imaging modality and for confocal imaging.

FIG. 3 illustrates an example image set that can be output by systems in accordance with the present technology. FIG. 3, for example, illustrates images of infiltrative BCC (basal cell carcinoma). As indicated, image a of FIG. 3 is a wide-field image of a region of concern. Images b-d of FIG. 3 are high resolution reflectance images of respective areas of the wide-field image of image a of FIG. 3, selected by an operator or computer, to be acquired. The relative positions of each of these areas can be seen from the white rectangles superimposed on image a. Similarly, images e-g of FIG. 3 are high-resolution fluorescence images of these same regions, respectively. The remaining images h and i are frozen histopathological samples used as a reference by the operator.

As can be seen, an operator can have an array of information at his or her fingertips on which to base a diagnosis. The operator can choose which imaging technique(s) to utilize, and can switch between images or imaging techniques, which greatly enhances operator efficiency.

The methods and systems of the present technology, as described above and shown in the drawings, provide for wide-field and high-resolution imaging with superior characteristics. It will be apparent to those skilled in the art that various modifications and variations can be made in the device and method of the present technology without departing from the spirit or scope of the invention. Thus, it is intended that the present invention include modifications and variations that are within the scope of the appended claims and their equivalents.

What is claimed is:

1. A device for wide-field and high resolution imaging of an object surface with registration, comprising:
   a first imaging modality having high resolution imaging means with a first observation line;
   a second imaging modality arranged in an image plane at a first angle with respect to an object plane, the second imaging modality having a second observation line and a wider imaging field than that of the first imaging modality; and
   a lens associated with the second imaging modality, arranged in a lens plane at a second angle with respect to the object plane, the second angle being equal to about one-half of the first angle,
   the first and second imaging modalities being mutually arranged such that the first and second observation lines intersect at a known point,
   wherein the first imaging modality is automatically positioned at a point of interest found with the second imaging modality.

2. The device of claim 1, wherein the first imaging modality includes a confocal microscope including an objective lens.

3. The device of claim 2, further comprising illumination means configured to provide illumination of an object through optics of the confocal microscope, the optics of the confocal microscope providing illumination for confocal microscopic images captured by the first imaging modality and images captured by the second imaging modality.

4. The device of claim 1, wherein the first imaging modality includes a multi-photon microscope.

5. The device of claim 1, wherein the first imaging modality includes a high-resolution CCD imaging device.

6. The device of claim 1, wherein the device is capable of adjusting to a first configuration, in which the second imaging modality is capable of capturing an image.

7. The device of claim 1, wherein the first imaging modality is capable of imaging beneath the object surface.

8. The device of claim 1, wherein the device is capable of adjusting to a second configuration, in which the first imaging modality is capable of capturing an image.

9. The device of claim 1, wherein the first and second imaging modalities are supported by a supporting structure.

10. The device of claim 9, wherein the second modality and the lens are pivotally supported by the device.

11. The device of claim 1, wherein the first angle is about 55 degrees.

12. The device of claim 1, wherein the second angle is about 27.5 degrees.

13. The device of claim 1, wherein the second imaging modality includes a CCD camera.

14. The device of claim 1, wherein the second imaging modality is capable of rotating about the observation line of the first imaging modality to facilitate imaging of the object surface.

15. The device of claim 1, wherein the second imaging modality is capable of multimodal imaging.

16. The device of claim 15, wherein imaging techniques for the multimodal imaging are selected from the group consisting essentially of reflectance, fluorescence, Raman, multiphoton and harmonic generation imaging.

17. The device of claim 1, wherein the object surface is tissue.

18. A device for wide-field and high resolution imaging of a point of interest on an object surface in an object plane, comprising:
   a light source having an illumination plane for illuminating the object surface;
   a narrow-field, high resolution imaging modality defining a first observation line and using the light source;
   a wide-field, low resolution imaging modality arranged in an image plane at a first angle with respect to the object plane, the second imaging modality defining a second observation line and using the light source; and
   a lens associated with the second imaging modality, arranged in a lens plane that substantially bisects the first angle,
   the first and second imaging modalities being optically coupled based upon a relative orientation of the first and second observation lines with respect to the illumination plane and the object plane such that the narrow-field, high resolution imaging modality is automatically positioned at the point of interest as found with the wide-field, low resolution imaging modality.

19. The device of claim 18, wherein the first and second observation lines intersect at a point substantially on the object plane.

20. The device of claim 18, further comprising a physical mounting structure to enable movement of the narrow-field, high resolution imaging modality and the wide-field, low resolution imaging modality over the object surface while pivotally moving the lens to maintain bisection of the first angle.

21. The device of claim 18, wherein the narrow-field, high resolution imaging modality is adjustable along the first observation line.

22. The device of claim 18, wherein the narrow-field, high resolution imaging modality and the wide-field, low resolution imaging modality share a common light source.

23. The device of claim 18, wherein the object surface is of tissue.

* * * * *

UNITED STATES PATENT AND TRADEMARK OFFICE
CERTIFICATE OF CORRECTION

PATENT NO. : 8,045,263 B2
APPLICATION NO. : 11/823610
DATED : October 25, 2011
INVENTOR(S) : Anna N. Yaroslavsky, Robert H. Webb and Richard R. Anderson Page 1 of 1

It is certified that error appears in the above-identified patent and that said Letters Patent is hereby corrected as shown below:

Title Page, Item (75) Inventors "Anna M. Yaroslavsky" should read -- Anna N. Yaroslavsky --

Signed and Sealed this
Second Day of October, 2012

David J. Kappos
*Director of the United States Patent and Trademark Office*